United States Patent

Denzel et al.

[11] 4,076,712
[45] Feb. 28, 1978

[54] DERIVATIVES OF PYRAZOLO[1,5-a]PYRIDO[2,3-d]PYRIMI-DIN-9(4H)-ONE

[75] Inventors: Theodor Denzel, Regensburg; Hans Hoehn, Tegernheim, both of Germany

[73] Assignee: E. R. Squibb & Sons, Inc., Princeton, N.J.

[21] Appl. No.: 783,253

[22] Filed: Mar. 31, 1977

[51] Int. Cl.² .................. C07D 471/14; A61K 31/415
[52] U.S. Cl. .............................. 260/256.4 F; 424/251
[58] Field of Search ................................. 260/256.4 F

[56] References Cited
U.S. PATENT DOCUMENTS

| | | |
|---|---|---|
| 3,150,136 | 9/1964 | Wolfrum et al. ............... 260/256.4 F |
| 3,171,740 | 3/1965 | Menzel et al. .................. 260/256.4 F |
| 3,787,408 | 1/1974 | Takamizawa et al. ......... 260/256.4 F |

*Primary Examiner*—Donald G. Daus
*Assistant Examiner*—James H. Turnipseed
*Attorney, Agent, or Firm*—Lawrence S. Levinson; Merle J. Smith

[57] ABSTRACT

New derivatives of pyrazolo[1,5-a]pyrido[2,3-d]pyrimidin-9(4H)-one and salts thereof have the general formula

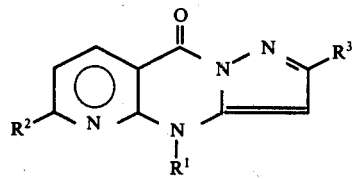

The compounds are useful as anti-inflammatory agents.

12 Claims, No Drawings

DERIVATIVES OF PYRAZOLO[1,5-A]PYRIDO[2,3-D]PYRIMIDIN-9(4H)-ONE

SUMMARY OF THE INVENTION

This invention relates to new derivatives of pyrazolo[1,5-a]pyrido[2,3-d]pyrimidin-9(4H)-one and salts thereof. These new compounds have the general formula

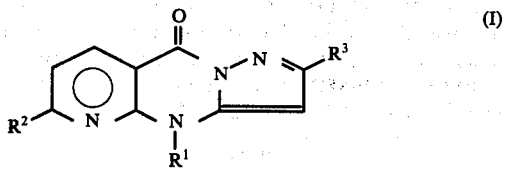

$R^1$ is hydrogen, lower alkyl or substituted lower alkyl, wherein the lower alkyl substituent is

$R^2$ is hydrogen or lower alkyl.
$R^3$ is hydrogen or lower alkyl.
$R^4$ and $R^5$ each is hydrogen or lower alkyl.

DETAILED DESCRIPTION OF THE INVENTION

The substituents represented by $R^1$, $R^2$, $R^3$, $R^4$ and $R^5$ in formula I have the following meanings throughout this specification.

The lower alkyl groups are straight or branched chain aliphatic hydrocarbon radicals having up to seven carbon atoms such as methyl, ethyl, propyl, isopropyl, butyl, isobutyl, t-butyl, amyl and the like. The $C_1$–$C_5$ alkyl groups are preferred.

The substituted lower alkyl groups are groups such as those above having as a substituent the group

These are the lower alkyl

groups such as amino-lower alkyl like aminomethyl, 2-aminoethyl and the like, lower alkylamino-lower alkyl like methylaminomethyl, (2-methylamino)ethyl, (2-methylamino)propyl, (3-methylamino)propyl, (2-ethylamino)ethyl and the like, di(lower alkyl)amino-lower alkyl like dimethylaminomethyl, (2-dimethylamino)ethyl, (2-diethylamino)ethyl, (3-dimethylamino)propyl and the like.

The products of the examples are representative of the various compounds of this invention.

The new compounds of formula I are formed by the following series of reactions.

A halonicotinic acid of the formula

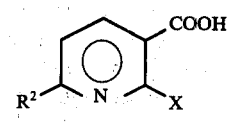

wherein X is halogen, especially chlorine, is made to react with an aminopyrazole of the formula

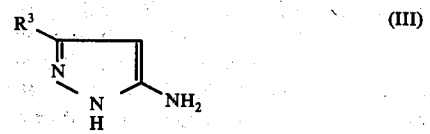

This reaction is accomplished in a high boiling solvent by heating the reactants at 200° to 220° C. By this reaction, compounds of the formula

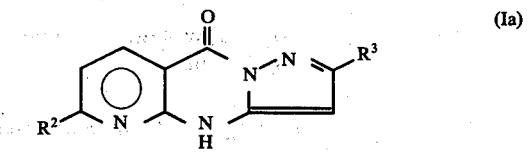

are obtained wherein $R^1$ is hydrogen.

Compounds of formula I, wherein $R^1$ is other than hydrogen, are now produced by reaction of compounds of formula Ia with the appropriate alkyl halide in the presence of an inorganic base like potassium carbonate, sodium hydroxide etc. in a solvent like dimethylformamide, acetone and the like.

The compounds of this invention form various salts which are also part of this invention. For example, when $R^1$ is hydrogen, such compounds will form salts with metals, e.g., alkali metals such as sodium or potassium or alkaline earth metals like calcium or magnesium, e.g., by reaction with a base like potassium hydroxide, potassium carbonate or the like. When there is an amine group present, e.g., the amine substituted lower alkyl groups, such compounds will form acid addition salts with inorganic or organic acids. Such acid addition salts include the hydrohalides, like hydrochloride, hydrobromide (which are preferred), other salts of inorganic acids like sulfate, phosphate, nitrate, borate, etc. Organic acid salts include, for example, tartrate, ascorbate, acetate, citrate, succinate, methanesulfonate, toluenesulfonate, etc. Physiologically acceptable members are preferred, however, other salts frequently provide a convenient means for isolating a product, e.g., by forming and precipitating the salt in an appropriate liquid in which the salt is insoluble, then after separation of the salt, neutralizing by conventional methods to obtain the free base. Other, physiologically acceptable salts can then be formed by reaction with an equivalent proportion of the appropriate acid or base, as the case may be.

The new compounds of this invention have antiinflammatory properties and are useful as antiinflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay or delayed hypersensitivity reaction assay in rats. The active substance is utilized in compositions such as tablets, capsules, solutions or suspensions containing up to about 300 mg. per unit of dosage of a compound or mixture of compounds of formula I or physiologically acceptable salt thereof. They are compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion or cream may also be used.

The following examples are illustrative of the invention and constitute especially preferred embodiments. They also serve as models for the preparation of other members of the group which can be produced by suitable substitution of starting materials. All temperatures are in degrees celsius.

EXAMPLE 1

2,4-Dimethylpyrazolo[1,5-a]pyrido[2,3-d]pyrimidin-9(4H)-one a.

2-Methylpyrazolo[1,5-a]pyrido[2,3-d]pyrimidin-9(4H)-one 157 g. of 2-chloropyridine-3-carboxylic acid and 194 g. of 5-amino-3-methylpyrazole are heated together in 500 ml. of diphenyl ether for 10 minutes at 215°. After this time, the mixture is allowed to stand at room temperature for 2 hours and is then filtered. The crystalline 2-methylpyrazolo[1,5-a]pyrido[2,3-d]pyrimidin-9(4H)-one is washed with methanol and recrystallized from dimethylformamide, yield: 120 g. (64%); m.p. >300°.

b.

2,4-Dimethylpyrazolo[1,5-a]pyrido[2,3-d]pyrimidin-9(4H)-one 3.8 g. of 2-methylpyrazolo[ 1,5-a]pyrido[2,3-d]pyrimidin-9(4H)-one are added to a solution of 1 g. of potassium hydroxide in 50 ml. of methanol and the mixture is stirred at room temperature for 2 hours. The potassium salt of 2-methylpyrazolo[1,5-a]pyrido[2,3-d]pyrimidin-9(4H)-one is filtered off and suspended in 25 ml. of diethyleneglycol dimethyl ether. 5 g. of methyl iodide are added and the mixture is stirred for 1 hour and then filtered off, and the precipitated 2,4-dimethylpyrazolo[1,5-a]pyrido[2,3-d]pyrimidin-9(4H)-one is recrystallized with methanol containing 10% water, yield: 2.1 g. (50%); m.p. 241.9°.

EXAMPLE 2

4-(3-Methylbutyl)pyrazolo[1,5-a]pyrido[2,3-d]pyrimidin-9(4H)-one a. Pyrazolo [1,5-a]pyrido[2,3-d]pyrimidin-9(4H)-one 15.7 g. of 2-chloropyridine-3-carboxylic acid and 16.6 g. of 5-aminopyrazole are heated carefully to about 180°. At this point, the reaction starts and the temperature rises to about 230°–240°. The mixture is allowed to cool to room temperature and is then treated with methanol. The undissolved pyrazolo[1,5-a]pyrido[2,3-d]pyrimidin-9(4H)-one is filtered off and recrystallized from dimethylformamide, yield: 10.5 g. (56%); m.p. >300°.

b.

4-(3-Methylbutyl)pyrazolo[1,5-a]pyrido[2,3-d]pyrimidin-9(4H)-one 1.8 g. of pyrazolo[1,5-a]pyrido[2,3-d]pyrimidin-9(4H)-one are suspended in 20 ml. of dimethylformamide. The addition of 2 g. of potassium carbonate provides the potassium salt (m.p. >300°). To this is added 2 g. of 1-bromo-3-methylbutane. The mixture is stirred at 80° for 24 hours. The insoluble precipitate is filtered off and the mother liquor evaporated to dryness. The residual 4-(3-methylbutyl)pyrazolo[1,5-a]pyrido[2,3-d]pyrimidin-9(4H)-one is recrystallized from butanol, yield: 1.4 g. (59%); m.p. 219.5°.

EXAMPLE 3

4-Methylpyrazolo[1,5-a]pyrido[2,3-d]pyrimidin-9(4H)-one 1.8 g. of pyrazolo[1,5-a]pyrido[2,3-d]pyrimidin-9(4H)-one are suspended in 10 ml. of methanol. 0.6 g. of potassium hydroxide are added and the mixture is stirred for 30 minutes. After this time, the potassium salt is filtered off and, after drying, suspended in 20 ml. of diethyleneglycol dimethyl ether. 2.5 g. of methyl iodide are added with stirring. After 20 minutes, 4-methylpyrazolo[1,5-a]pyrido[2,3-d]pyrimidin-9(4H)-one is filtered off, washed with water and recrystallized from methanol, yield: 1.1 g. (55%); m.p. 249.2°.

EXAMPLE 4

[4-(2-Dimethylamino)ethyl]pyrazolo[1,5-a]pyrido[2,3-d]pyrimidin-9(4H)-one 1.5 g. of 2-dimethylaminoethyl-1-chloride, 1.8 g. of pyrazolo[1,5-a]pyrido[2,3-d]pyrimidin-9(4H)-one and 1.5 g. of potassium carbonate are stirred together in 20 ml. of dimethylformamide for 24 hours at 80°. The inorganic precipitate is filtered off and the mother liquor is evaporated to dryness. The remaining oil is extracted three times with hot benzene. After evaporation of the benzene, the residual [4-(2-dimethylamino)ethyl]pyrazolo[1,5-a]pyrido[2,3-d]pyrimidin-9(4H)-one is recrystallized from ethyl acetate, yield: 1.1 g. (43%); m.p. 113°–115°. Treatment with ethanolic HCl gives the hydrochloride salt.

EXAMPLE 5

2,6-Dimethylpyrazolo[1,5-a]pyrido[2,3-d]pyrimidin-9(4H)-one 17.1 g. of 2-chloro-6-methylpyridine-3-carboxylic acid and 19.4 g. of 5-amino-3-methylpyrazole are heated together for 10 minutes at 180°–190°. The mixture is cooled to room temperature and treated with methanol. The crystalline 2,6-dimethylpyrazolo[1,5-a]pyrido[2,3-d]pyrimidin-9(4H)-one is filtered off and recrystallized from dimethylformamide, yield: 13.5 g. (64%); m.p. >300°.

EXAMPLE 6

6-Methylpyrazolo[1,5-a]pyrido[2,3-d]pyrimidin-9(4H)-one 17.1 g. of 2-chloro-6-methylpyridine-3-carboxylic acid and 16.6 g. of 5-aminopyrazole are heated together at 180°–190° for 10 minutes. The mixture is cooled to room temperature and treated with methanol. The crystalline 6-methylpyrazolo[1,5-a]pyrido[2,3-d]pyrimidin-9(4H)-one is filtered off and recrystallized from dimethylformamide, yield: 11.3 g. (56%); m.p. >300°.

EXAMPLE 7

4-(3-aminopropyl)pyrazolo[1,5-a]pyrido[2,3-d]pyrimidin-9(4H)-one

By substituting 3-chloropropylamine for 2-dimethylaminoethyl-1-chloride in the procedure of Example 4, 4-(3-aminopropyl)pyrazolo[1,5-a]pyrido[2,3-d]pyrimidin-9(4H)-one is obtained

EXAMPLE 8

4-(Methylaminomethyl)pyrazolo[1,5-a]pyrido[2,3-d]pyrimidin-9(4H)-one

By substituting methylaminomethyl chloride for the 2-dimethylaminoethyl-1-chloride in the procedure of Example 4, 4-(methylaminomethyl)pyrazolo[1,5-a]pyrido[2,3-d]pyrimidin-9(4H)-one is obtained.

What is claimed is:

1. A compound of the formula

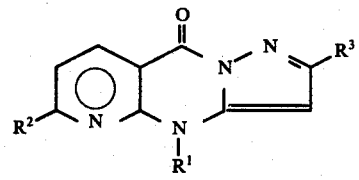

wherein $R^1$ is hydrogen, lower alkyl or -lower alkyl

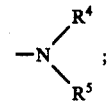

$R^2$, $R^3$, $R^4$ and $R^5$ each is hydrogen or lower alkyl; and salts physiologically acceptable thereof.

2. A compound as in claim 1 wherein $R^1$, $R^2$ and $R^3$ each is hydrogen or lower alkyl.

3. A compound as in claim 1 wherein $R^1$ is di(lower alkyl)amino-lower alkyl.

4. A compound as in claim 1 wherein $R^1$ is -lower alkyl $$-N\begin{matrix}R^4\\R^5\end{matrix}$$

and $R^4$ and $R^5$ each is hydrogen or lower alkyl.

5. A compound as in claim 1 wherein $R^1$ and $R^2$ each is hydrogen and $R^3$ is methyl.

6. A compound as in claim 1 wherein $R^1$, $R^2$ and $R^3$ each is hydrogen.

7. A compound as in claim 1 wherein $R^1$ and $R^3$ each is hydrogen and $R^2$ is methyl.

8. A compound as in claim 1 wherein $R^1$ is hydrogen and $R^2$ and $R^3$ each is methyl.

9. A compound as in claim 1 wherein $R^1$ is methyl and $R^2$ and $R^3$ each is hydrogen.

10. A compound as in claim 1 wherein $R^1$ is 3-methylbutyl and $R^2$ and $R^3$ each is hydrogen.

11. A compound as in claim 1 wherein $R^1$ and $R^3$ each is methyl and $R^2$ is hydrogen.

12. A compound as in claim 1 wherein $R^1$ is dimethylaminoethyl and $R^2$ and $R^3$ each is hydrogen.

* * * * *